United States Patent
Bakke et al.

(10) Patent No.: US 11,268,057 B2
(45) Date of Patent: Mar. 8, 2022

(54) APPARATUS AND METHOD FOR TREATMENT OF WET ORGANIC MATTER TO PRODUCE BIOGAS

(71) Applicants: Universitetet i Sørøst-Norge, Kongsberg (NO); Waterment AS, Porsgrunn (NO); Yara International ASA, Oslo (NO)

(72) Inventors: Rune Bakke, Skien (NO); Dag Normann Øvrebø, Oslo (NO)

(73) Assignees: UNIVERSITETET I SØRØST-NORGE, Kongsberg (NO); WATERMENT AS, Porsgrunn (NO); YARA INTERNATIONAL ASA, Oslo (NO)

( * ) Notice: Subject to any disclaimer, the term of this patent is extended or adjusted under 35 U.S.C. 154(b) by 262 days.

(21) Appl. No.: 16/477,212

(22) PCT Filed: Jan. 17, 2018

(86) PCT No.: PCT/NO2018/050010
§ 371 (c)(1),
(2) Date: Jul. 11, 2019

(87) PCT Pub. No.: WO2018/135952
PCT Pub. Date: Jul. 26, 2018

(65) Prior Publication Data
US 2019/0359921 A1    Nov. 28, 2019

(30) Foreign Application Priority Data
Jan. 18, 2017    (NO) .................................. 20170077

(51) Int. Cl.
*C12M 3/00*    (2006.01)
*C12F 3/00*    (2006.01)
(Continued)

(52) U.S. Cl.
CPC ......... *C12M 21/04* (2013.01); *B01D 21/0033* (2013.01); *B01D 21/0051* (2013.01);
(Continued)

(58) Field of Classification Search
CPC ............................ C12M 29/08; C12M 27/24
See application file for complete search history.

(56) References Cited

U.S. PATENT DOCUMENTS

| | | | |
|---|---|---|---|
| 2,083,348 A * | 6/1937 | Scholler | ................. C12M 23/34 |
| | | | 435/295.2 |
| 4,521,310 A | 6/1985 | Casey | |

(Continued)

FOREIGN PATENT DOCUMENTS

| | | |
|---|---|---|
| CA | 2 723 334 A1 | 11/2008 |
| DE | 36 04 415 A1 | 8/1987 |

(Continued)

OTHER PUBLICATIONS

Zupancic et al., Bioresource Technology, 2008, vol. 99, p. 100-109.*

(Continued)

*Primary Examiner* — Nathan A Bowers
(74) *Attorney, Agent, or Firm* — Amster, Rothstein & Ebenstein LLP

(57) ABSTRACT

Apparatus for treatment of wet organic matter to produce biogas, comprising a closed reactor (11) for anaerobic digestion of the wet organic matter. The anaerobic reactor comprises two vertical 5 tubes, a vertically arranged outer tube (14) defining a first reactor chamber (111) enveloping a vertically arranged inner tube (15) which is divided into a first region (112*a*) and a second region (112*b*) of a second reactor chamber (112) by a vertical partitioning wall (16). The first reactor chamber comprises a particle retaining unit (31) connecting the first and the second reactor chambers.

(Continued)

The anaerobic reactor (11) exhibits a top discharge pipe (18) for gas developed in either 0 of the two reactor chambers (111, 112). A method for treatment of wet organic matter is also contemplated.

13 Claims, 6 Drawing Sheets

(51) Int. Cl.
    *B01D 21/00* (2006.01)
    *C12M 1/107* (2006.01)
    *B01D 21/24* (2006.01)
    *C02F 3/22* (2006.01)
    *C02F 3/28* (2006.01)
    *C02F 11/04* (2006.01)
    *C12M 1/00* (2006.01)
    *C12P 5/02* (2006.01)

(52) U.S. Cl.
    CPC ..... *B01D 21/0087* (2013.01); *B01D 21/2444* (2013.01); *B01D 21/2494* (2013.01); *C02F 3/22* (2013.01); *C02F 3/284* (2013.01); *C02F 11/04* (2013.01); *C12M 23/34* (2013.01); *C12M 23/58* (2013.01); *C12M 27/18* (2013.01); *C12M 29/24* (2013.01); *C12M 41/14* (2013.01); *C12P 5/023* (2013.01); *C02F 2203/006* (2013.01)

(56) References Cited

U.S. PATENT DOCUMENTS

| | | | |
|---|---|---|---|
| 4,983,517 A * | 1/1991 | Kim | B01J 8/222 422/156 |
| 5,637,220 A | 6/1997 | Buisman | |
| 2005/0109694 A1 | 5/2005 | You | |
| 2006/0243661 A1 | 11/2006 | You et al. | |
| 2007/0251880 A1 * | 11/2007 | Herding | C02F 3/101 210/603 |
| 2008/0248552 A1 * | 10/2008 | Castillo Fernandez | B01F 13/0827 435/243 |
| 2011/0168021 A1 | 7/2011 | Vellinga et al. | |
| 2012/0156744 A1 * | 6/2012 | Macdonald | C12M 23/58 435/155 |
| 2017/0101612 A1 * | 4/2017 | Kleppen | C12M 21/08 |
| 2019/0263694 A1 * | 8/2019 | Yang | C02F 3/2846 |

FOREIGN PATENT DOCUMENTS

| | | |
|---|---|---|
| EP | 0 102 610 A1 | 3/1984 |
| EP | 2 065 344 A1 | 6/2009 |
| GB | 2 167 055 A | 5/1986 |
| WO | 94/29227 A1 | 12/1994 |

OTHER PUBLICATIONS

PCT International Search Report and Written Opinion dated Apr. 26, 2018 in connection with PCT International Application No. PCT/NO2018/050010.

Norwegian Search Report dated Jul. 20, 2017 in connection with Norwegian Patent Application No. 20170077.

* cited by examiner

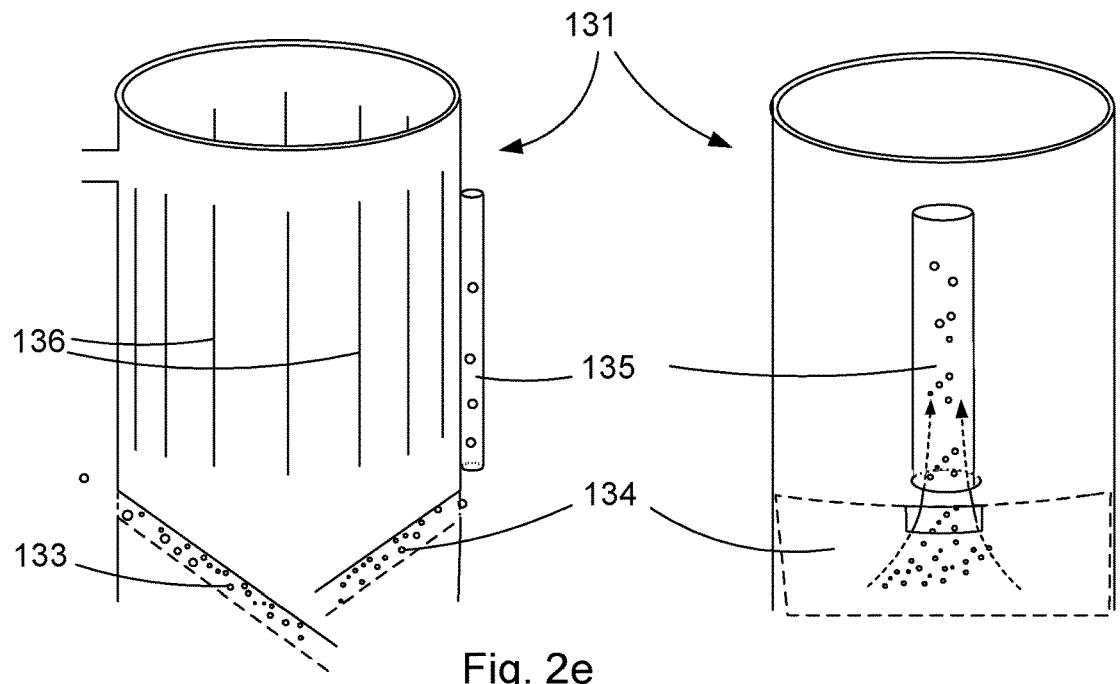
Fig. 2e
Fig. 2f
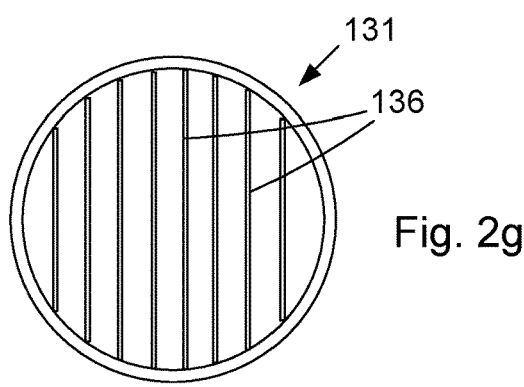
Fig. 2g
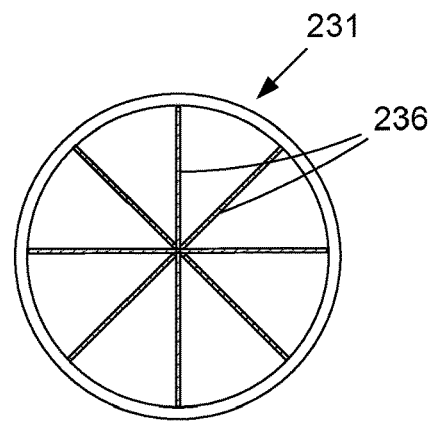
Fig. 2h
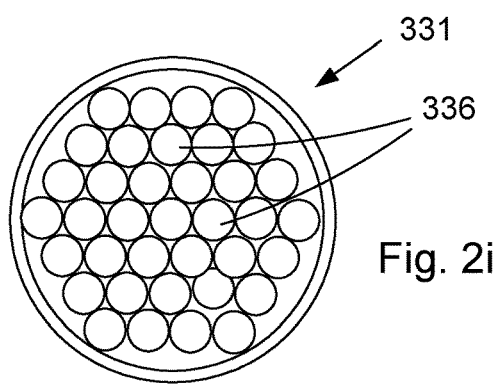
Fig. 2i

APPARATUS AND METHOD FOR TREATMENT OF WET ORGANIC MATTER TO PRODUCE BIOGAS

CROSS-REFERENCE TO RELATED APPLICATIONS

This application is a U.S. national stage entry under 35 U.S.C. § 371 of PCT International Patent Application No. PCT/NO2018/050010, filed Jan. 17, 2018, which claims priority to Norwegian Patent Application No. 20170077, filed Jan. 18, 2017, the contents of which are incorporated herein by reference in their entirety.

FIELD OF THE INVENTION

The present relates to the design of a process to recover resources from wet organic wastes, such as energy, nutrients and organics from manure, sludge, slurries and wastewater. More precisely the present invention relates to an apparatus for treatment of wet organic matter to produce biogas according to the preamble of claim 1 and method for treatment of wet organic matter comprising a mixture of fluid and solid particulates according to the preamble of claim 13.

BACKGROUND

Wet organic wastes (WOW) are to an increasing extent used as source for biogas production by anaerobic digestion (AD) through processes that also yield other products such as nutrient that can be used as fertilizer. The bioreactor technology available for AD often represents a capital cost that is not covered by the value of the products produced, making the implementation of such solutions dependent on idealism and/or government subsidies. More efficient bio processes are therefore required to make AD processes more sustainable and industrially feasible. Additional downstream treatment is often needed to comply with discharge limits and improve the quality of produced gas, organics and fertilizers. The cost of such treatment can be quite high. There is thus a need for an advanced bioprocess to improve production efficiency and product quality, to cut investment and operational costs.

A number of methods and systems/apparatuses have been proposed in this technical field. Anaerobic sludge blanket reactors (UASB) have been used for high rate anaerobic digestion processes but are not suitable for particle rich fluids such as slurries, cf. Tchobanoglous, G., Burton, F. L., & Stensel, H. (2003). *Wastewater Engineering: Treatment and reuse, Advanced Wastewater Treatment, 4th Edition*. McGraw-Hill Series in Civil and Environmental Engineering. Metcalf and Eddy Inc. New York.

An anaerobic baffle reactor (ABR) is described in U.S. Pat. No. 5,091,315 (McCarty, 1989). McCarty teaches a bioconversion reactor for anaerobic fermentation of organic material comprising a shell enclosing a defined volume, an inlet port through which a liquid stream of organic material can enter the reactor as well as an outlet port through which the material may leave the reactor. A series of vertical and spaced-apart baffle plates are arranged in the reactor forcing the stream to pass under and over the plates respectively.

The anaerobic baffle reactors (ABR) were originally designed to take advantage of the UASB principles while being able to handle feeds with high particulates contents but it has not been very successful since it is not as efficient as intended.

Other methods and devices in this technical field are described in CN 106242162 A (2016); WO 16059621 A (Alessandro, 2016); WO 16050893 A1 (Uller, 2016); WO 15037989 A1 (Koorneef, 2015); RU 2536988 C (Burdin et al., 2013); WO 13112182 A1 (Smith, 2013).

Still, the general challenge of providing cost-effective and space-effective methods and apparatuses in this technical field remains.

OBJECTIVE

It is an objective of the present invention to provide a method and an apparatus to treat organic sludge from industry and agriculture, wastewater and other types of wet organic wastes, more efficiently than available solutions through a novel bioreactor process design, producing methane at a moderate cost.

It is a further objective of the invention to provide an apparatus suited for conducting such a method, with low mechanical complexity and construction cost.

Finally, it is an objective to provide the above mentioned method and apparatus to convert organic wastes into valuable, non-toxic products that require little and inexpensive post-treatment.

THE PRESENT INVENTION

The above objects are fulfilled with the apparatus and method according to the present invention.

According to a first aspect, the invention relates to an apparatus as defined by claim 1.

According to a second aspect the invention concerns a method as defined by claim 13. The dependent claims disclose preferred embodiments of the invention.

The apparatus of the invention comprises an anaerobic reactor comprising two reactor chambers where an inner reactor chamber is enveloped within an outer reactor chamber. In a general perspective this is a known concept. Within this particular field and with the specific design here presented, the design is unique and inventive, due to the inherent advantages.

In a preferred embodiment the apparatus of the present invention also includes a second reactor arranged downstream of the anaerobic reactor, said second reactor being arranged as an aerobic reactor.

In the following description, if not otherwise specifically is stated, the term "methane" is meant to cover pure methane as well as biogas in which methane is the main constituent.

"Pipe" as used herein, refers to a tubular section or hollow cylinder, typically but not necessarily of circular cross-section. In particular the inner tubes of the reactors may have polygonal cross-sections, such as a square cross-section. Independent thereof, the innermost tube of the aerobic reactor, if present, may also have a cross-section selected among polygonal cross-sections, circular cross-section, and oval cross-sections.

Further and preferred details of the apparatus and method are provided in the detailed description below with reference to the enclosed drawings.

FIG. 1b is a schematic and simplified top sectional view of the apparatus of FIG. 1a.

FIG. 2b is a schematic and simplified top sectional view of the apparatus of FIG. 2a.

FIG. 2e is an enlarged sectional side view of a detail 131 slightly different from detail 31 shown in FIG. 2c.

FIG. 2f is a perspective view of elements shown in FIG. 2e.

FIGS. 2g-2i are top sectional views of different embodiments of details 31, 131 in FIGS. 2c-2f.

It should be noted that the dimensions may be distorted on the drawings; e.g. the ratio between diameter and height for the various equipment shown.

Since the present invention is related to a method as well as an apparatus, parts of the drawings are referred to with slightly different terminology depending on whether the apparatus or the method is discussed. Thus, one and the same figure detail may be referred to as "reactor chamber" when discussing apparatus and as "reaction zone" when discussing method; as "conduit" when discussing apparatus and as "process flow" when discussing method.

Figure 1A:
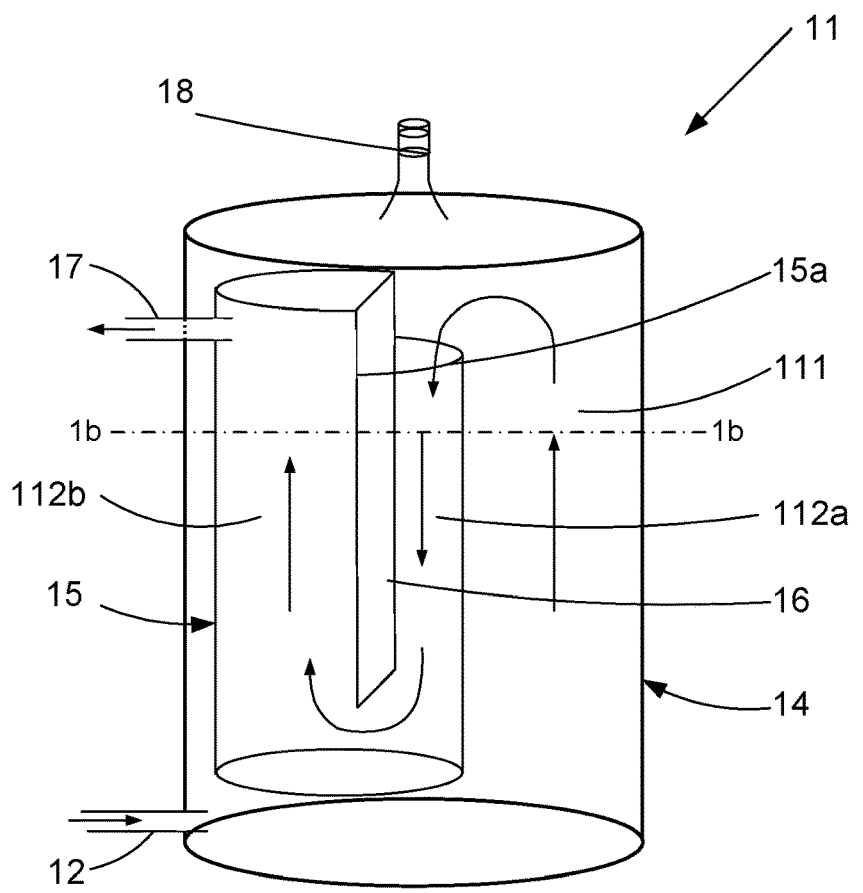
FIG. 1a is a schematic and simplified side transparent perspectival view of an apparatus on which the present invention is based.

FIG. 1a is a schematic view of an apparatus on which the present invention is based, showing a reactor 11 comprising a closed outer cylinder 14 and an inner cylinder 15 completely enveloped by the outer cylinder. By "closed" is understood that the cylinder has a fluid tight bottom and a fluid tight top, with exception of the shown inlet and outlet conduits. This design is applicant's own design but lacks the characterizing features of the present invention. It has not been publically shown.

Fresh material to be treated is to be charged to the first and outer reactor chamber 111 via inlet conduit 12, the outer reactor chamber being defined between the inner wall of the outer cylinder and the outer wall of the inner cylinder.

The inner cylinder has a top end a vertical distance below the top of the outer cylinder and a bottom end a vertical distance above the bottom of the outer cylinder. The inner cylinder shown in FIG. 1a has a wall section 15a, the top of which is lower than the top of the inner cylinder, thereby allowing material flow from the outer cylinder over the top of said low wall 15a into a first region 112a of the inner cylinder adjacent to said low wall section 15a. Said region 112a of the inner cylinder is partly separated from the other region 112b of the inner cylinder by a vertical plate or partition wall 16 which extends downwards from the top of the inner cylinder 15 and which is terminated a distance above the closed bottom wall of the inner cylinder.

It is imperative for the economy of the process as well as for the operational conditions that the discharge flow from the reactor 11 is a flow of substantially particle free fluid and that the particles are retained until converted to gas through the action of microorganisms.

While the plate or partition wall 16 extends from the top of the inner cylinder 15, it is typically not attached to the top in a fluid tight manner. More preferably a space is left open along the top of the partition wall 16 or through perforations in the uppermost section of it to allow produced gas to pass through to reach a common gas discharge conduit 18.

The arrangement described above allows transportation flow of material from the bottom to the top of the outer cylinder 14, downwards in the region 112a of the inner cylinder and upwards again in the region 112b of the inner cylinder. It is desired, however, that the material leaving the reactor 11 through the conduit 17 arranged near the top of region 112b of the inner cylinder, is solely fluid material and that all particles of the material remain in the apparatus until converted to gas from the action of microorganisms, anaerobic bacteria or archaea.

Methane containing biogas developed by the action of the microorganisms, is arranged to leave the reactor through a conduit 18 arranged at the top of the reactor 11. Since methane is developed in the inner cylinder as well as in the outer cylinder, the top of the inner cylinder may be open to allow flow of methane containing biogas to the conduit 18 or provided with a separate gas discharge conduit (not illustrated).

Figure 1B:
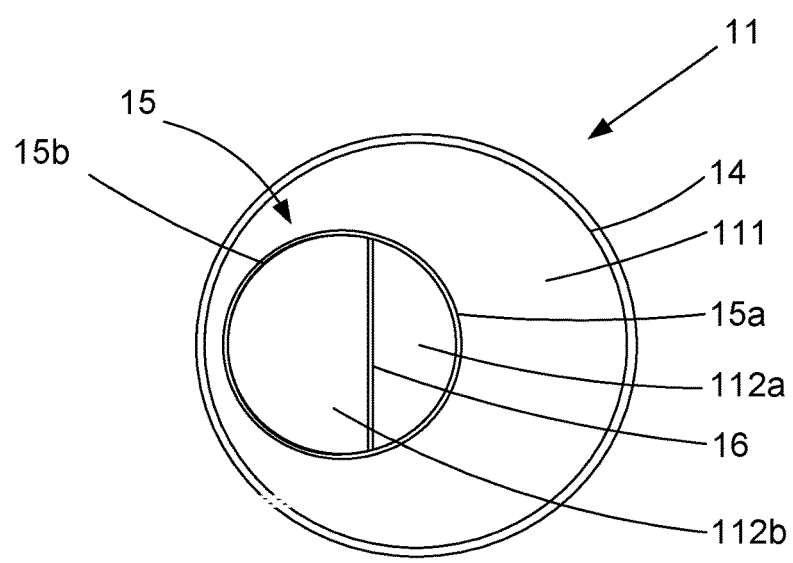

FIG. 1b is a top sectional view of the reactor 11 shown in FIG. 1, illustrating the outer cylinder 14, the inner cylinder 15, the first reactor chamber 111 defined by the inner wall of the outer cylinder and the outer wall of the inner cylinder, the first region 112a of the second reactor chamber and the second region 112b of the second reactor chamber, said regions being separated by a vertical partition wall 16 extending from the top of the inner cylinder down to a bottom edge located above the bottom wall of the inner cylinder.

Figure 1C:
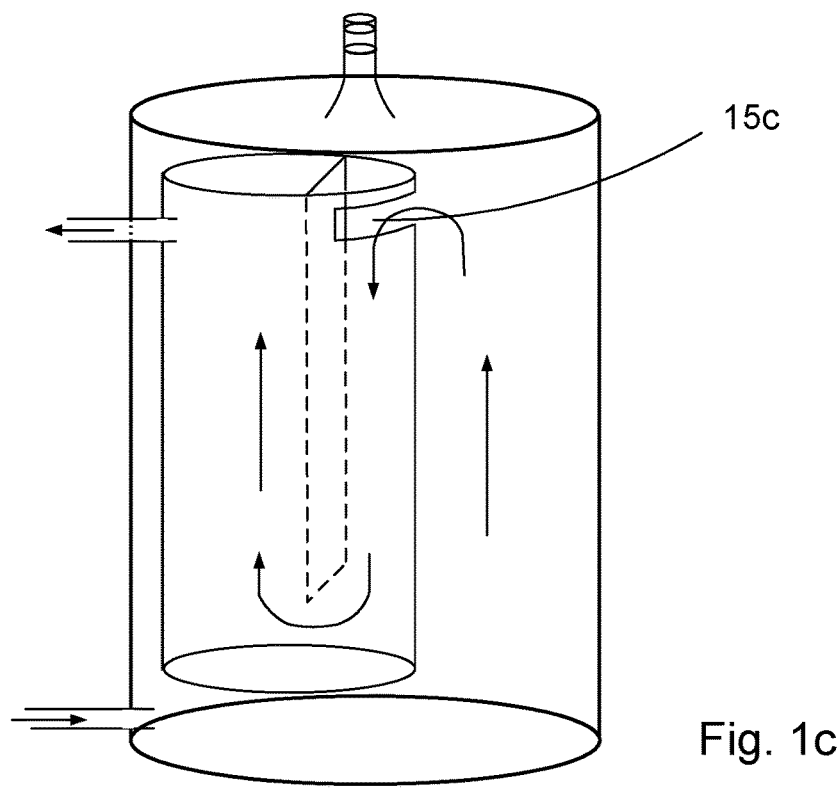
FIG. 1c is a schematic and simplified side transparent perspectival view of an apparatus which is slightly different from the one shown in FIG. 1a FIG. 2a is a schematic and simplified side transparent perspectival view of a preferred embodiment of the apparatus according to the present invention.

FIG. 1c shows an anaerobic reactor principally similar to the one discussed in relation to FIG. 1a above. The sole difference between these designs is that the open passage from the first, outer reactor chamber into the first section 112a of the inner reactor chamber has the form of a slot opening 15c in the vertical wall rather than a completely open section adjacent to a lower wall section 15a in such a way that fluid flowing from compartment 111 to 112a is discharged from compartment 111 below the upper fluid surface of compartment 111. The feed conduit 12, the discharge conduit 17 and the internal flow between these are all as described above.

It is difficult if not impossible to retain all the particulate material in the apparatus as shown in FIGS. 1a-1c, therefore, according to the present invention, additional equipment are incorporated in the anaerobic reactor 11 as discussed below.

Figure 2A:
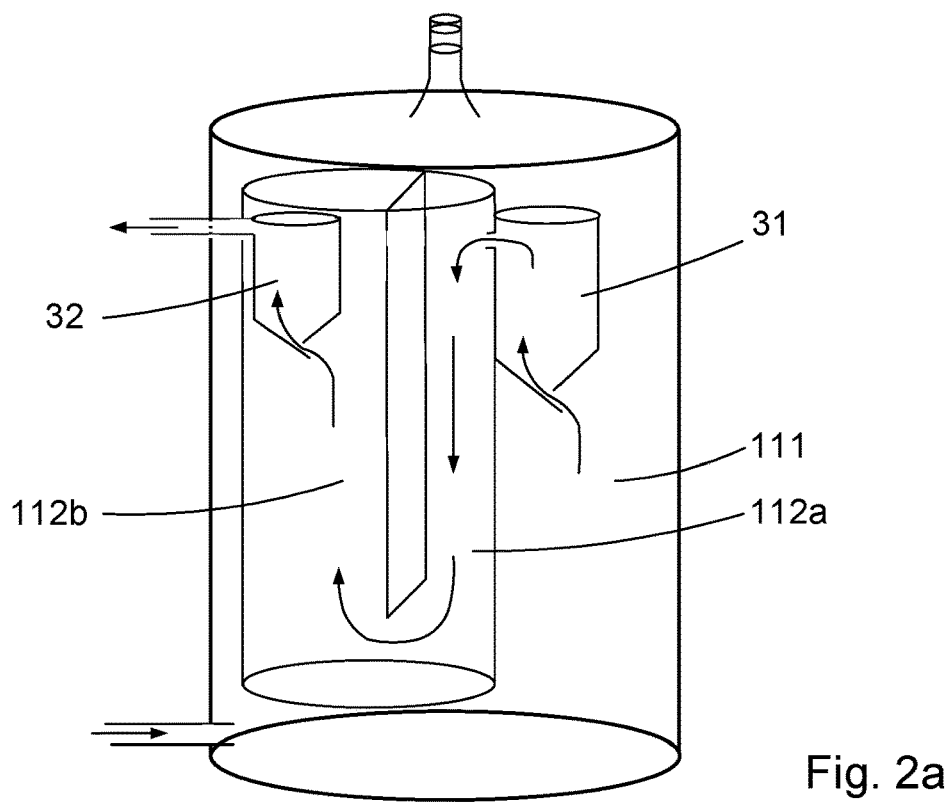

A separator or particle retaining unit 31 is arranged near the top of the outer cylinder 14, cf. FIG. 2a, constituting a particle trap passage through which the fluid has to flow before entering region 112a of the inner cylinder. In a similar manner a separator 32 may be arranged near the top of the inner cylinder 15, between the second reactor chamber 112 and the discharge conduit 17, through which separator fluid has to flow before leaving the reactor 11. These separators 31, 32 have the function of retaining as much as possible of the solid, particulate material in each of the cylinders until being converted to gas by the action of the microorganisms.

Figure 2B:
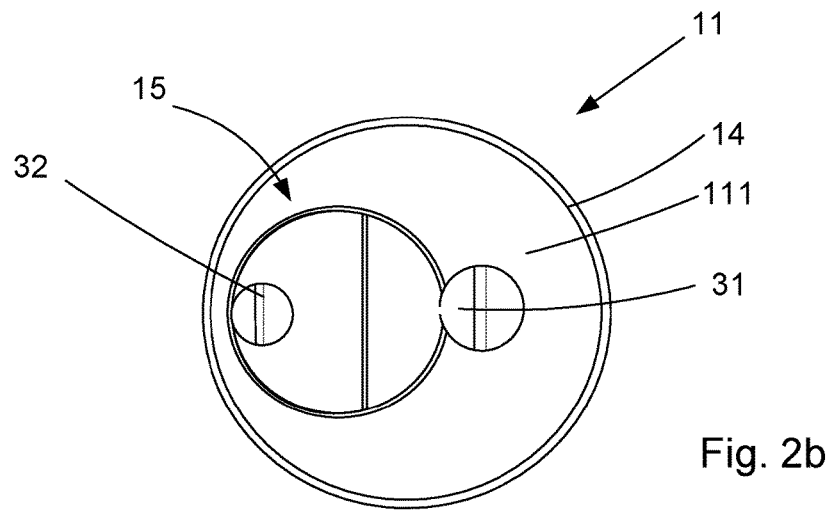

FIG. 2b is a top sectional view of the embodiment shown in FIG. 2a.

Figure 2C:
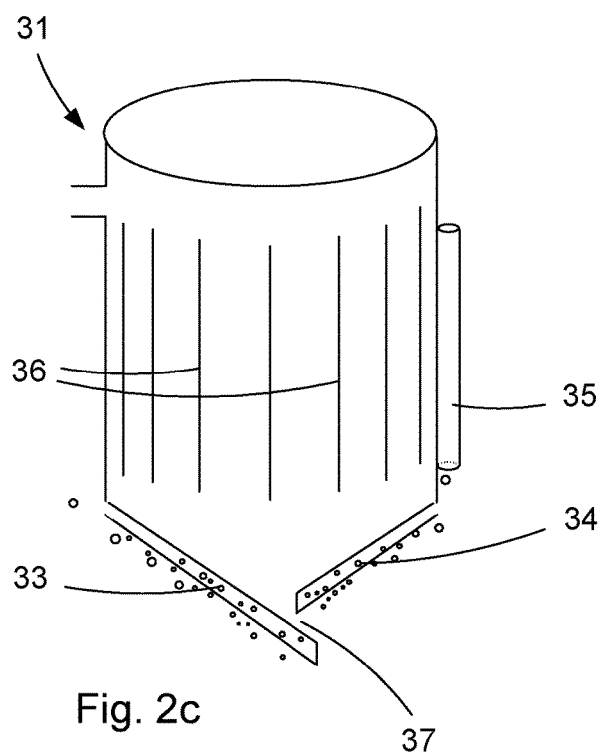
FIG. 2c is an enlarged sectional side view of a detail 31 from FIGS. 2a and 2b.

Now referring to FIG. 2c, such particle retaining units (e.g. 31) may be supplied with arrangements at the lower surfaces that gather small rising gas bubbles into larger bubbles as they flow along the lower surfaces towards the highest point of these lower surfaces. This can be achieved by having a downward pointing rim on these surfaces to channel the bubbles to the highest points of each surface, where there is an opening to direct where the bubbles are released for further vertical flow towards the upper fluid surface. In FIG. 2c, inclined regions 33 and 34 are arranged to direct vertically rising bubbles carrying small solid particles away from the entrance of the separator 31 so as to prevent the particles to escape the reaction chamber with the fluid. At least one mainly vertically arranged pipe 35 may be used to convey such accumulated bubbles and particles to the top of the reaction chamber in question or they may flow freely upwards outside the separator 31. To enter the separator 31 through the slot shaped entrance 37, the fluid has to move in a mainly horizontal direction, while the lighter gas bubbles tends to rise vertically past the entrance.

Inside the particle retaining unit 31 may be provided with vertically extending partition walls 36 to ensure a mainly laminar upwards flow of fluid in the unit.

Figure 2D:
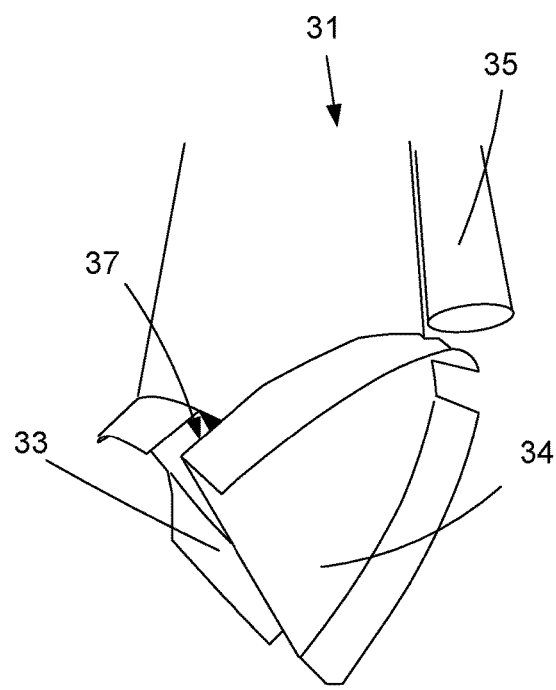
FIG. 2d is a perspective view of elements shown in FIG. 2c.

FIG. 2d provides a perspective view of part of the particle retaining unit 31 shown in FIG. 2c, is a direction slightly upwards. The inclined regions or elements 33 and 34 are shown with a downwards extending rim, contributing to direct the gas bubbles upwards to ports in the rim arranged at their highest points. A port in the rim surrounding inclined region 34 is so positioned that most of the bubbles escaping the region will enter the optional pipe 35. The slot shaped entrance 37 for liquid to the particle retaining unit is just barely visible on the drawing due to the partly overlap horizontally of the inclined regions 33 and 34.

FIG. 2e shows an embodiment of a particle retaining unit 131 slightly different from the embodiment 31 of FIG. 2c, the main difference being that the outer cylindrical wall of the unit 131 is extended to at least partly cover the inclined regions 133, 134 and that the opening for the gas bubbles at the upper end of inclined region 134 has the form of a hole in the cylindrical wall rather than a recess in a rim.

The embodiment of FIG. 2e is shown from a different angle in FIG. 2f, the hole in the cylindrical wall and the pipe 135 facing the viewer. Dotted lines in FIG. 2f illustrate the path for bubbles moving upwards along the inclined region 134 (dotted lines) hidden by the outer cylindrical wall of the particle retaining unit (below the entrance opening for the liquid), passing through the hole in the wall to the outside and from there passing into the lower entrance of the pipe 135, still rising upwards.

FIG. 2g is a top sectional view of the interior of particle retaining unit 131, showing a number of parallel partition walls 136 making the fluid entering to flow mainly laminar therethrough. FIG. 2h shows a top sectional view of the interior of particle retaining unit 231, showing a number of partition walls 236 arranged diametrically, still making the fluid entering to flow mainly laminary therethrough. FIG. 2i shows a top sectional view of the interior of particle retaining unit 331, showing a number of partition walls 336 having the form of a stack of pipes having a diameter significantly smaller than that of the particle retaining unit 331. Also In this case the fluid entering the particle retaining unit is made to flow mainly laminary therethrough.

The purpose of gathering small bubbles into large ones before they rise to the reactor liquid surfaces in such a way that they locally impose strong mixing is to break up floating sludge at the upper fluid surface to enhance release of gas within this floating sludge and allow such sludge to settle faster to lower sections of the reactor chambers. These larger bubbles may flow freely along the sides of the particle retaining units (31, 32) or in a pipe ending close to the fluid surface.

Such particle retaining units 31, 32 may also be supplied with inside arrangements consisting of parallel plates or tubes parallel to the said units side walls to dampen flow disturbances and obtain laminar flow conditions to enhance sedimentation of particles.

The reactor chamber 111 may be provided with any suitable temperature controlling device in order to monitor and control the temperature therein.

It is also an option to include such a separator in just one of the cylinders, e.g. just a separator 32 in the inner cylinder. Each separator may be a technically simple device, such as a mainly cylindrical body provided with inclined plates extending into the area through which the material tends to move, to retard the upwards motion thereof and preferably to impose one or more directional change of motion and also to lengthen the travel distance from the inlet conduit to the outlet conduit for one or both of the reaction chambers 111, 112. The shape of the separator should be such that particles floating upwards due to entrapped gas bubbles will be diverted by the inclined plates to not enter the separator but rather float to the top, from where it will settle back down by gravity when entrapped gas has been released. More complex separators may include plural plates or the like to impose several directional changes for the fluid on its way to the discharge.

Figure 3:
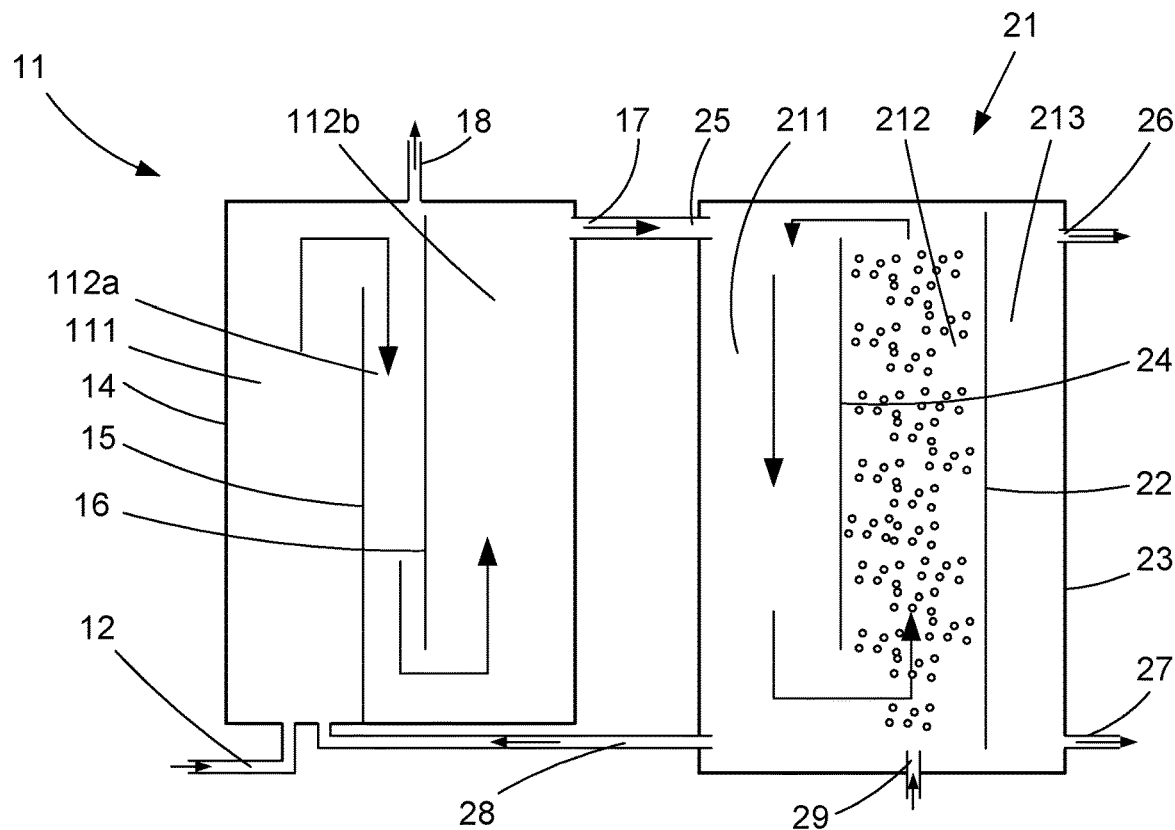
FIG. 3 is a principle view of a preferred embodiment of the process according to the present invention.

Reference is now made to FIG. 3 which is more oriented to process than to apparatus design. In another preferred embodiment, independent of the presence of separators, a second reactor 21 is arranged downstream of the first anaerobic reactor. The second reactor is arranged as an aerobic reactor and has at least a function in purifying the discharge water from the first reactor. It may also have the function of supporting and improving the digestion conditions in the first reactor, by means of a recycle of fluid from the second reactor to the first reactor. The second reactor may be designed in a number of ways, the common denominator being an arrangement in which air or oxygen or oxygen enriched air is brought into intimate contact with the fluid for a period of time sufficient for oxygen to be absorbed by the water so that microorganisms in the reactor can take up sufficient oxygen to cause bio-chemical reaction between oxygen and components in the fluid, such as in particular methane and organic components.

The second reactor 21 comprising at least two reactor chambers 211, 212, the first reactor chamber 211 of which being arranged to receive as feed the material discharged trough discharge conduit 17 of the first reactor, the second reactor chamber 212 being arranged for addition of oxygen though an inlet conduit 29, and a recycle conduit 28 for recycling fluid with particulate material from the aerobic reactor 21 to the anaerobic reactor 11, while an optional third reactor chamber 213 of the second reactor exhibits an upper discharge conduit 26 for purified fluid and a lower discharge conduit 27 for mostly particulate matter.

In a preferred embodiment the aerobic reactor 21 may, instead of a third reactor chamber 213, be provided with a particle retaining unit between the reactor chambers 211 and 212 and optionally one at the discharge conduit 26.

The recycle conduit 28 is typically provided with means to control the flow rate therethrough independently of other flow rates through the reactor chambers.

Figure 4:
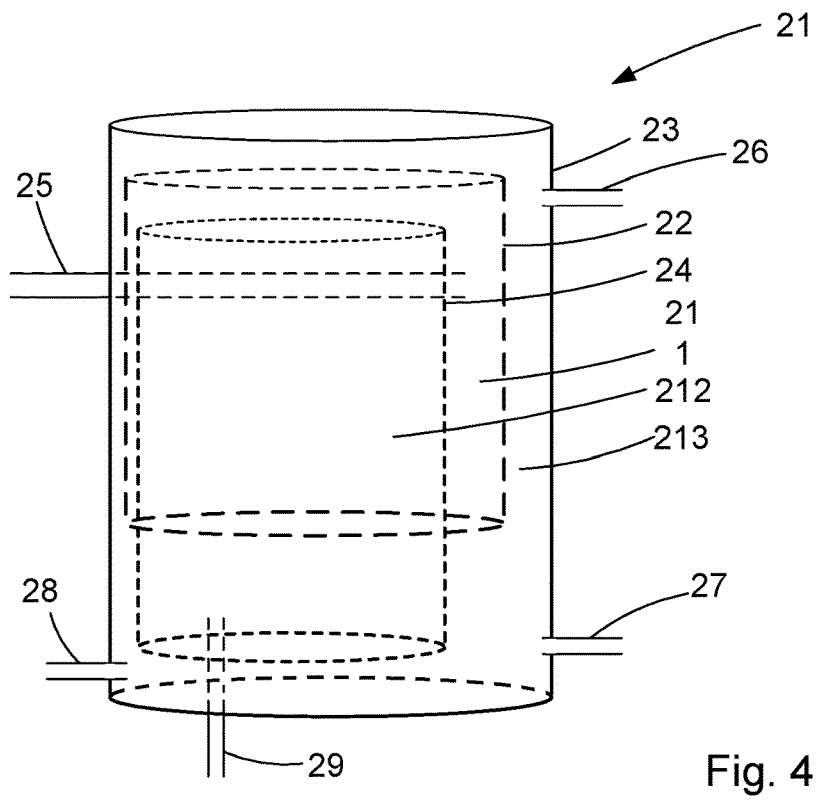
FIG. 4 is a schematic and simplified side transparent perspectival view of an embodiment of the optional aerobic reactor.

Reference is now made to FIG. 4. The second reactor may, similar to the first reactor, be designed as tubes in tube. More specifically, the first reactor chamber 211 of the second reactor 21 may be defined within an inner, open vertical tube 22 while the third reactor chamber 213 may be defined between an outer, closed vertical tube 23 and such inner vertical tube 22.

Specifically, the second reactor 21 may be comprised by three reactor chambers 211, 212, 213 separated by vertical walls having the shape of an open innermost tube 24 arranged within a wider inner tube 22, both of which being arranged within a still wider closed vertical tube 23, the upper wall edge of the innermost tube 24 being terminated below the fluid discharge conduit 26 that determines the fluid level in the closed vertical tube 23. The lower wall of the innermost tube 24 is terminated above the bottom of the outer, closed vertical tube 23 while the upper wall edge of the wider inner tube (22) is terminated above the fluid discharge conduit 26 that determines the fluid level in the closed vertical tube 23. The lower wall of the wider inner tube 22 is terminated above the bottom of the outer, closed vertical tube 23, thus defining an annulus 211 between the inside wall of tube 22 and the outside wall of tube 24 and defining an annulus 213 between the inside wall of tube 23 and the outside wall of tube 22.

FIG. 3 is a schematic view of the process according to the method constituting the second aspect of the present invention. It should be noted that FIG. 3 does not intend to illustrate any specific design of the reactors or reactor chambers involved, only the methodology. Thus, the process taking place in the left hand part of FIG. 3 may very well be conducted in a reactor of the type illustrated in the previously discussed drawings.

To the left the feed fluid flows through a reactor in which an anaerobic digestion process takes place. Organic material/sludge to be treated is supplied through conduit 12 at the bottom of a first reactor chamber 111. Microorganisms, mainly anaerobic bacteria and archaea are present in a sludge bed in reactor 11 to facilitate conversion to methane in a manner known per se. The fluid part of the feed passes over the partition wall 15, optionally through a separator. The partition wall 15 may be the wall of an inner cylinder enveloped by an outer cylinder as earlier described.

From here the fluid flows downwards and into a reaction zone or chamber 112a, under the partition wall and upwards in reactor chamber 112b. The fluid then flows through a discharge conduit 17, optionally after having passed through a separator (not shown), from the first reactor 11 connected to an inlet conduit 25 into the second reactor 21 near the top of 21. The second reactor is arranged as an aerobic reactor and comprises three reactor chambers or reaction zones 211, 212, 213, which are at least partially separated from one another as explained below. In a first reaction zone 211 of the aerobic reactor 21, the flow direction is downwards. In the second reaction zone 212 the flow direction is upwards, facilitated by addition of air, oxygen enriched air or pure oxygen gas through an inlet conduit 29. There will be interaction by continuous circulation between the zones 211 and 212, which are only partly separated by a partition wall 24 having open passages below its lower side edge and above its upper side edge. The aeration in zone 212 supplies the oxygen required i.a. for microorganisms to carry out bio-chemical reaction between oxygen and components such as methane and organic components in the fluid. Particles may be collected at the bottom of zone 211 and recycled to the anaerobic reactor 11 along with some amounts of fluid, e.g. through recycle conduit 28, to improve anaerobic performance by increased biogas production and improved biogas quality.

Treated fluid leaves the zone 212 to zone 213 under the partition wall 22 partly separating zone 212 from 213. Zone 213 serves as a sedimentation zone to retain particles. Particles can be harvested at the bottom of zone 213 and discharged through outlet conduit 27.

MAIN FEATURES AND ADVANTAGES

The new invention combines the best aspects of UASB and ABR, simplifying the ABR design so as to make its construction much cheaper and to enable more efficient retention of particles, comparable that of standard ABR designs.

Furthermore, the preferred integrated anaerobic and aerobic process enhances the transformation of organic matter to methane beyond what is obtainable by an anaerobic process alone. The aerobic processes in reactor 21 capture and convert remaining dissolved organic matter and dissolved inorganic matter in the anaerobic effluent to biomass through growth of aerobic microorganisms through biochemical reactions using oxygen as electron acceptor. Part of the fluid in the aerobic reactor is pumped back to the anaerobic reactor in a controlled manner to supply aerobic biomass as extra feed for methane production in the anaerobic reactor.

Such aerobic biomass can have an additional benefit on the anaerobic process since it can contain more and different enzymes than the purely anaerobic culture, thereby enhancing hydrolysis of particles in the feed, also leading to more and faster biogas production.

The oxygen containing bubbles introduced in chamber 212 induce upwards fluid flow in 212 which will again induce a downward fluid flow in 211 where the effluent from the anaerobic reactor is introduced, allowing dissolved gasses in the introduced fluid to be absorbed in the aerobic reactor fluid while the fluid is flowing downwards, allowing time for methane to be taken up by the organisms, thereby preventing methane from being stripped off as a greenhouse gas downstream of the anaerobic reactor. Dissolved methane in the fluid is consumed and used as feed for growth by aerobic micro-organisms so that there is no dissolved methane in the fluid when it enters 212 at the bottom, thereby avoiding stripping off of methane to the atmosphere with the air bubbles that are introduced in chamber 212.

Dissolved $CO_2$ in the fluid introduced in 211 has no role as feed for aerobic biomass growth and will not be taken up, so it will be stripped off to the atmosphere when the fluid enters 212 with the air bubbles that are introduced there. The fluid recycled from 21 to 11 is thereby low in $CO_2$, so that the methane to $CO_2$ ratio of the biogas recovered from the anaerobic reactor is higher than what will be achieved in 11 without such process interaction with 21. Combining 11 and 21 thereby serves as a principle for internal biogas upgrading since methane is the desired product.

Particles that are heavier than water are separated by gravity from the water that flows upwards in 213 towards the effluent conduit 26 and are thereby retained in the process to maintain a high concentration of micro-organisms to carry out the required processes and to make nutrient rich agglomerates that can be harvested as products and to avoid particles in the treated water. The a separator or particle retaining unit, such as 31 and 32 in FIG. 2a can serve the same purpose as Chamber 213 as an alternative to retain agglomerated particles in 21. Surplus agglomerates can be harvested from reactor 11 and/or 21, to obtain different quality agglomerates.

While the process conducted by means of the aerobic reactor is shown generally as material moving from left to right, a convenient design of the reactor may also in this case have the form of vertical cylinders enveloping one another, in this case cylinder within cylinder within cylinder, as principally illustrated by FIG. 4 and commented above.

The microbiological cultures used according to the present invention are typically present as suspended microbiological cultures, or as attached microbiological cultures or as a combination thereof.

The anaerobic process may be conducted as up-flow anaerobic sludge beds, implying that the culture is retained by gravity when the fluid leaves the chambers.

Dissolved methane in the fluid in reaction zone 211 is consumed by aerobic micro-organisms so that there is no dissolved methane in the fluid when it enters reaction zone 212, thereby avoiding stripping off of methane to the atmosphere with the air bubbles that are introduced in reaction zone 212.

Dissolved $CO_2$ in the fluid introduced in reaction zone 211 may be stripped off to the atmosphere when the fluid enters reaction zone 212 with the air bubbles that are introduced in reaction zone 212 so that the fluid recycled 28 from the aerobic process 21 to the anaerobic process 11 is low in $CO_2$, thereby facilitating a high methane to $CO_2$ ratio of the biogas produced in the anaerobic process.

The fluid leaving the process as treated water has to flow upwards in the third reaction zone 213 allowing particles that are heavier than water to be separated by gravity from the water and thereby be retained in the process to maintain a high concentration of micro-organisms to carry out the required processes and to make nutrient rich agglomerates that can be harvested as products and to maintain high level of organic nutrient rich agglomerates in recycle conduit 28 and to avoid particles in the treated water.

The anaerobic process of the present invention may generally be conducted in any number of up-flow anaerobic sludge beds wherein a particle retaining unit is arranged between each up-flow anaerobic sludge bed chamber and the discharge of said chamber.

EXAMPLE

Figure 5:
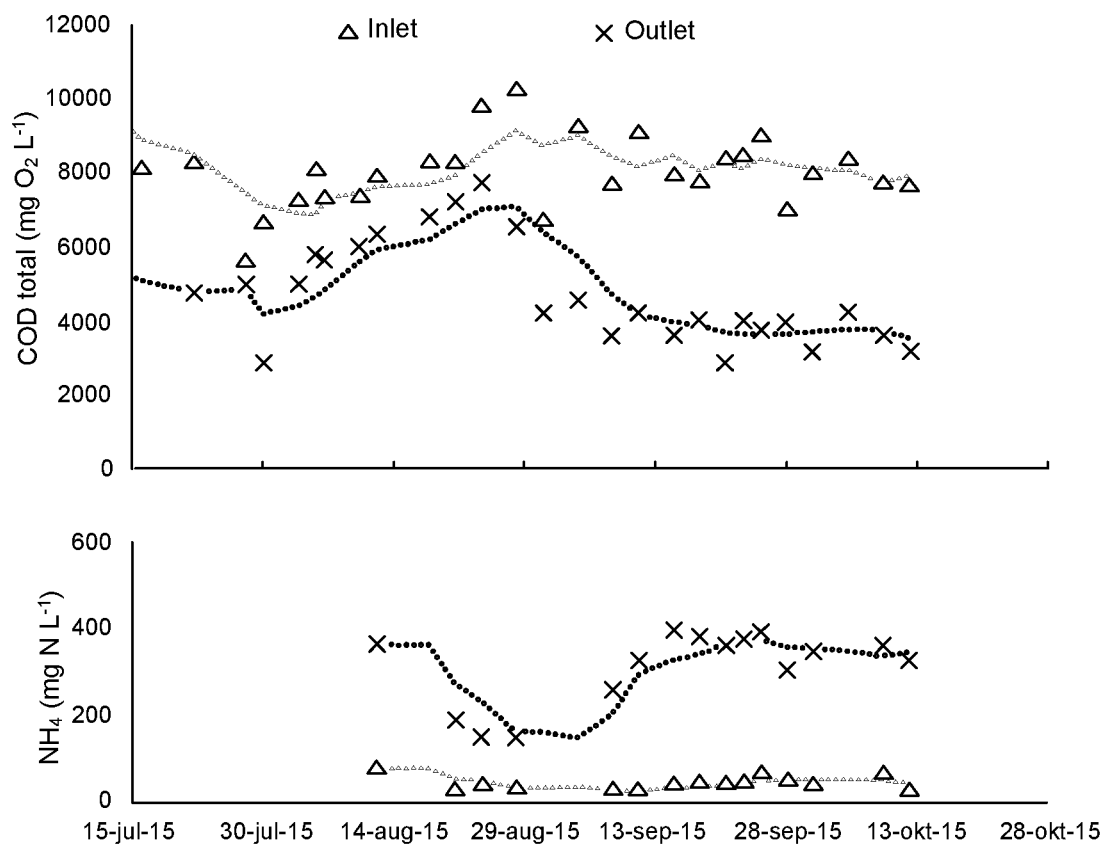
FIG. 5 shows graphs of chemical oxygen demand (COD) and $NH_4$ respectively at inlet and outlet during a practical example.

A pilot plant constructed according to FIG. 1 have been tested for several months using particle rich "Black water" from vacuum toilets as feed. The first graph of FIG. 5 shows the development of organic matter removal, as chemical oxygen demand (COD) in and out of the reactor, measured according to standard procedures and equipment supplied by Hach, Manchester, GB. Measurements were taken regularly from start-up 15 Jul. 2015 until 13 Oct. 2015 and show that more than half of the feed COD was removed when the process reach steady state conditions towards the end of the test period. Ammonium is released when organic matter that contains proteins is broken down, as can be seen in the second graph where the measured outlet ammonium level is several times higher than inlet concentrations at steady state, confirming efficient degradation of organic matter in the reactor design. Several other measurements, such as pH, organic acids, biogas production and biogas composition also confirm that the process functions as intended.

https://en.wikipedia.org/wiki/Blackwater (waste): Blackwater is used to describe wastewater containing feces, urine and flushwater from flush toilets along with anal cleansing water (if water is used for cleansing) or toilet paper,[1] It is distinct from greywater or sullage, the wastewater generated from washing food, clothes, and dishware, as well as from bathing, but not from toilets.

The invention claimed is:

1. Apparatus for treatment of wet organic matter to produce biogas, comprising a first reactor (11) for anaerobic digestion of the wet organic matter, wherein said first reactor (11) is an anaerobic reactor, and wherein said first reactor (11) has the form of two vertical tubes, a vertically arranged outer tube (14) defining a first reactor chamber (111) enveloping a vertically arranged inner tube (15) which is divided into a first region (112a) and a second region (112b) of a second reactor chamber (112) by a vertical partitioning wall (16) leaving a free area between the first region (112a) and the second region (112b) near the bottom of the inner tube (15) to allow material transportation therethrough, the upper end of the first region (112a) of the second reactor chamber exhibiting an opening to first reactor chamber (111) for allowing material transportation from the first reactor chamber (111) to the first region (112a) of the second reactor chamber (112), said first reactor chamber (111) being connected to an inlet conduit (12) at its lower end while the second reactor chamber (112b) at its upper end is connected to a discharge conduit (17) for fluid material, the first reactor (11) further exhibiting a top discharge pipe (18) for gas developed in either of the two reactor chambers (111, 112), characterized in that a first particle retaining unit (31) is arranged between the first reaction chamber (111) and the first region (112a) of the second reactor chamber (112), wherein the first particle retaining unit (31) is supplied with arrangements at the lower surfaces that gather small rising gas bubbles into larger bubbles and channel these to rise to the reactor liquid surfaces in such a way that they locally impose strong mixing to break up floating sludge to enhance release of gas within this floating sludge.

2. Apparatus as claimed in claim 1, wherein the opening between the first section of the second reactor chamber (112) and the first reactor chamber (111) has the form of a slot shaped opening (15c) in the wall section of the inner tube at the first region (112a) thereof.

3. Apparatus as claimed in claim 1, wherein a second particle retaining unit (32) is arranged between the second reactor chamber (112) and the discharge conduit (17).

4. Apparatus as claimed in claim 1, wherein the larger bubbles flow from where they were gathered in a pipe ending at or close to the fluid surface.

5. Apparatus as claimed in claim 1, wherein the first particle retaining unit (31) is supplied with inside arrangements consisting of parallel plates or tubes parallel to the said unit's side walls to dampen flow disturbances and obtain laminar flow conditions to enhance sedimentation of particles.

6. Apparatus as claimed in claim 1, wherein the first reactor chamber (111) is provided with a temperature controlling device.

7. Apparatus as claimed in claim 1, wherein the apparatus furthermore comprises a second reactor (21) arranged downstream of the first reactor (11), wherein the second reactor (21) is a closed aerobic reactor and wherein the second reactor comprises a fluid inlet conduit (25) connected to the fluid discharge conduit (17) from the first reactor (11), the second reactor (21) comprising at least two reactor chambers (211, 212), the first reactor chamber (211) of the second reactor (21) being arranged to receive as feed the material discharged through discharge conduit (17) of the first reactor, the second reactor chamber (212) being arranged for addition of oxygen though an inlet conduit (29), and a recycle conduit (28) for recycling fluid with particulate material from the second aerobic reactor (21) to the first reactor (11).

8. Apparatus as claimed in claim 7, wherein the second reactor (21) further comprises a third reactor chamber (213) exhibiting an upper discharge conduit (26) for purified fluid and a lower discharge conduit (27) for mostly particulate matter or wherein the second reactor (21) further comprises a third particle retaining unit arranged between the reactor chamber (211 or 212) and the discharge conduit (26).

9. Apparatus as claimed in claim 7, wherein the recycle conduit (28) for recycling particulate matter and fluid from the second reactor (21) to the first reactor (11) is arranged for adjustable flow amounts.

10. Apparatus as claimed in claim 8, wherein the first reactor chamber (211) of the second reactor (21) is defined within an inner, open vertical tube (22) and the third reactor chamber (213) is defined between an outer, closed vertical tube (23) and said inner vertical tube (22).

11. Apparatus as claimed in claim 7, wherein the second reactor (21) is comprised by three reactor chambers (211, 212, 213) separated by vertical walls having the shape of an open innermost tube (24) arranged within a wider inner tube (22), both of which being arranged within a wider closed vertical tube (23), the upper wall edge of the innermost tube (24) being terminated below the fluid discharge conduit (26) that determines the fluid level in the closed vertical tube (23), the lower wall of the innermost tube (24) being terminated above the bottom of the outer, closed vertical tube (23), the upper wall edge of the wider inner tube (22) being terminated above the fluid discharge conduit (26) that determines the fluid level in the closed vertical tube (23), the lower wall of the wider inner tube (22) being terminated above the bottom of the outer, closed vertical tube (23), defining an annulus (211) between the inside wall of tube (22) and the outside wall of tube (24) and defining an annulus (213) between the inside wall of tube (23) and the outside wall of tube (22).

12. Apparatus as claimed in claim 3, wherein the second particle retaining unit (32) is supplied with arrangements at the lower surfaces that gather small rising gas bubbles into larger bubbles and channel these to rise to the reactor liquid surfaces in such a way that they locally impose strong mixing to break up floating sludge to enhance release of gas within this floating sludge.

13. Apparatus as claimed in claim 3, wherein the second particle retaining unit (32) is supplied with inside arrangements consisting of parallel plates or tubes parallel to the said unit's side walls to dampen flow disturbances and obtain laminar flow conditions to enhance sedimentation of particles.

* * * * *